(12) United States Patent
Green et al.

(10) Patent No.: US 9,335,316 B2
(45) Date of Patent: *May 10, 2016

(54) BISPHENOL A COMPOUNDS USEFUL AS MARKERS FOR LIQUID HYDROCARBONS AND OTHER FUELS AND OILS

(75) Inventors: George D. Green, Cary, IL (US); Raymond J. Swedo, Mount Prospect, IL (US); Robert Butterick, III, Swedesboro, NJ (US)

(73) Assignees: Rohm and Haas Company, Philadelphia, PA (US); Dow Global Technologies LLC, Midland, MI (US)

( * ) Notice: Subject to any disclaimer, the term of this patent is extended or adjusted under 35 U.S.C. 154(b) by 203 days.

This patent is subject to a terminal disclaimer.

(21) Appl. No.: 14/124,780

(22) PCT Filed: Jun. 19, 2012

(86) PCT No.: PCT/US2012/043137
§ 371 (c)(1),
(2), (4) Date: Dec. 9, 2013

(87) PCT Pub. No.: WO2012/177632
PCT Pub. Date: Dec. 27, 2012

(65) Prior Publication Data
US 2014/0179955 A1    Jun. 26, 2014

Related U.S. Application Data

(60) Provisional application No. 61/499,247, filed on Jun. 21, 2011.

(51) Int. Cl.
| | |
|---|---|
| *C07C 43/205* | (2006.01) |
| *G01N 33/28* | (2006.01) |
| *G01N 33/22* | (2006.01) |
| *C10L 1/00* | (2006.01) |
| *C10L 1/185* | (2006.01) |
| *C10M 129/16* | (2006.01) |

(52) U.S. Cl.
CPC ........ *G01N 33/2882* (2013.01); *C07C 43/2055* (2013.01); *C10L 1/003* (2013.01); *C10L 1/1852* (2013.01); *C10M 129/16* (2013.01); *G01N 33/22* (2013.01); *C10M 2207/04* (2013.01); *C10N 2240/56* (2013.01)

(58) Field of Classification Search
None
See application file for complete search history.

(56) References Cited

U.S. PATENT DOCUMENTS

| 7,858,373 B2 | 12/2010 | Banavali et al. |
| 2006/0275700 A1 | 12/2006 | Lee et al. |

FOREIGN PATENT DOCUMENTS

| JP | 1983093752 A | 6/1983 |
| JP | 1983076446 A | 11/1984 |
| JP | 1985120830 A | 6/1985 |
| JP | 2001302619 A | 10/2001 |
| WO | 2012177614 A1 | 12/2012 |

OTHER PUBLICATIONS

Barton et al., "The Synthesis and characterization of vinyl-terminated oligomeric ethers", Polymer, vol. 30, Issue 8, pp. 1546-1551, Aug. 1989.*
Douglas, et al., "Synthesis of acetylene-terminated monomers: 1,1'-(1-methylethylidene)bis[4-(4-ethynylphenyl)methoxy]benzene 1,3-bis[(4-ethynyl phenoxy)methyl]benzene", Polymer, Elsevier Science, B.V. GB, vol. 35, No. 20, pp. 4462-4464 (1994).
Dalla Cort, et al., "Experimental and computational study of complexes between quats and naphthalenophanes", Supra. Chem., vol. 13, No. 2, pp. 313-323 (2001).
Douglas, et al., "Curing Reactions in Acetylene Terminated Resins-III. DSC, TGA and TMA Study of Catalyzed Cure of an Ethynylaryl-Terminated Monomer", Eur. Polym. J., vol. 29, No. 11, pp. 1513-1519 (1993).
Xiong, et al., "A one-pot approach to dendritic star polymers via double click reactions", Polym. Bull. vol. 65, pp. 455-463 (2010).

* cited by examiner

*Primary Examiner* — Rosalynd Keys
(74) *Attorney, Agent, or Firm* — Kenneth Crimaldi

(57) ABSTRACT

A compound having formula (I),

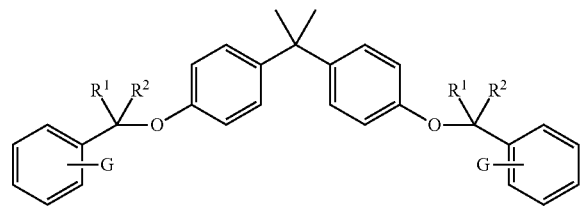

(I)

wherein $R^1$ and $R^2$ independently represent hydrogen or $C_1$-$C_4$ alkyl groups, and G represents hydrogen or at least one substituent selected from the group consisting of $C_1$-$C_{18}$ alkyl and $C_1$-$C_{18}$ alkoxy; provided that when $R^1$ and $R^2$ represent hydrogen, G does not represent hydrogen, 4-methyl, 4-methoxy, 3-methoxy, 2,6-dipropargyl, 4-vinyl, 4-ethynyl or 3-ethynyl.

9 Claims, No Drawings

BISPHENOL A COMPOUNDS USEFUL AS MARKERS FOR LIQUID HYDROCARBONS AND OTHER FUELS AND OILS

This invention relates to compounds useful in a method for marking liquid hydrocarbons and other fuels and oils.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, U.S. Pat. No. 7,858,373 discloses the use of a variety of organic compounds for use in marking liquid hydrocarbons and other fuels and oils. However, there is always a need for additional marker compounds for these products. Combinations of markers can be used as digital marking systems, with the ratios of amounts forming a code for the marked product. Additional compounds useful as fuel and lubricant markers would be desirable to maximize the available codes. The problem addressed by this invention is to find additional markers useful for marking liquid hydrocarbons and other fuels and oils.

STATEMENT OF INVENTION

The present invention provides a compound having formula (I),

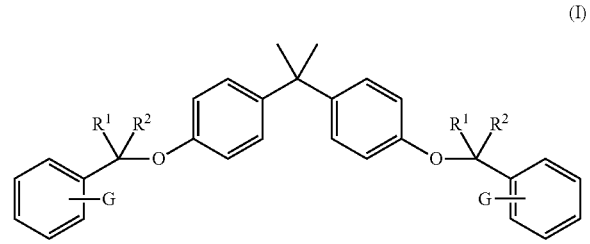

wherein $R^1$ and $R^2$ independently represent hydrogen or $C_1$-$C_4$ alkyl groups, and G represents hydrogen or at least one substituent selected from the group consisting of $C_1$-$C_{18}$ alkyl and $C_1$-$C_{18}$ alkoxy; provided that when $R^1$ and $R^2$ represent hydrogen, G does not represent hydrogen, 4-methyl, 4-methoxy, 3-methoxy, 2,6-dipropargyl, 4-vinyl, 4-ethynyl or 3-ethynyl.

DETAILED DESCRIPTION

Percentages are weight percentages (wt %) and temperatures are in ° C., unless specified otherwise. Concentrations are expressed either in parts per million ("ppm") calculated on a weight/weight basis, or on a weight/volume basis (mg/L); preferably on a weight/volume basis. The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon or a liquid biologically derived fuel; examples of the latter are biodiesel fuel, ethanol, butanol, ethyl tert-butyl ether or mixtures thereof. A substance is considered a liquid if it is in the liquid state at 20° C. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol." An "alkyl" group is a substituted or unsubstituted hydrocarbyl group having from one to twenty-two carbon atoms in a linear or branched arrangement. An "alkyl" group may have double or triple bonds. Substitution on alkyl groups of one or more hydroxy or alkoxy groups is permitted. Preferably, alkyl groups are saturated and unsubstituted. Preferably, the compounds of this invention contain elements in their naturally occurring isotopic proportions.

G represents hydrogen or at least one substituent selected from the group consisting of $C_1$-$C_{18}$ alkyl and $C_1$-$C_{18}$ alkoxy, i.e., each aromatic ring bearing a "G" substituent in formula (I) is unsubstituted or has at least one substituent selected from the group consisting of $C_1$-$C_{18}$ alkyl and $C_1$-$C_{18}$ alkoxy. Preferably, when G is not hydrogen it represents one to three substituents on each aromatic ring, which may be the same or different, preferably one or two substituents, preferably two or three substituents, preferably one or two identical substituents, preferably two or three identical substituents. However, the substituents represented by "G" are the same on the two aromatic rings substituted by G, i.e., the compound is symmetric with a plane of symmetry between the benzene rings of the central biphenyl moiety. Preferably, G represents hydrogen or at least one substituent selected from the group consisting of $C_1$-$C_{12}$ alkyl and $C_1$-$C_{12}$ alkoxy, preferably $C_1$-$C_8$ alkyl and $C_1$-$C_8$ alkoxy, preferably $C_1$-$C_6$ alkyl and $C_1$-$C_6$ alkoxy, preferably $C_1$-$C_6$ saturated alkyl and $C_1$-$C_6$ saturated alkoxy, preferably $C_1$-$C_4$ saturated alkyl and $C_1$-$C_4$ saturated alkoxy, preferably $C_1$-$C_4$ saturated alkyl, preferably $C_1$-$C_3$ saturated alkyl, preferably methyl and ethyl. Preferably, $R^1$ and $R^2$ independently represent hydrogen, methyl or ethyl; preferably hydrogen or methyl. Preferably, $R^1$ is methyl and $R^2$ is hydrogen, preferably $R^1$ and $R^2$ both are hydrogen. Preferably, G does not represent hydrogen. Preferably, G does not represent a single substituent in the 4-position. Preferably, when $R^1$ and $R^2$ represent hydrogen, G represents at least one saturated alkyl group, preferably not in the 4-position. Preferably, when $R^1$ and $R^2$ represent hydrogen, and G represents a single saturated alkyl group at the 4-position, the saturated alkyl group is a $C_3$-$C_8$ alkyl group In using the compounds of this invention as markers, preferably the minimum amount of each compound added to a liquid to be marked is at least 0.01 ppm, preferably at least 0.02 ppm, preferably at least 0.05 ppm, preferably at least 0.1 ppm, preferably at least 0.2 ppm. Preferably, the maximum amount of each marker is 50 ppm, preferably 20 ppm, preferably 15 ppm, preferably 10 ppm, preferably 5 ppm, preferably 2 ppm, preferably 1 ppm, preferably 0.5 ppm. Preferably, the maximum total amount of marker compounds is 100 ppm, preferably 70 ppm, preferably 50 ppm, preferably 30 ppm, preferably 20 ppm, preferably 15 ppm, preferably 12 ppm, preferably 10 ppm, preferably 8 ppm, preferably 6 ppm, preferably 4 ppm, preferably 3 ppm, preferably 2 ppm, preferably 1 ppm. Preferably, a marker compound is not detectible by visual means in the marked petroleum hydrocarbon or liquid biologically derived fuel, i.e., it is not possible to determine by unaided visual observation of color or other characteristics that it contains a marker compound. Preferably, a marker compound is one that does not occur normally in the petroleum hydrocarbon or liquid biologically derived fuel to which it is added, either as a constituent of the petroleum hydrocarbon or liquid biologically derived fuel itself, or as an additive used therein.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., *J. Pharm. Sci.*, vol. 84, pp. 83-92 (1995). Preferably the petroleum hydrocarbon or liquid biologically derived fuel is a petroleum hydrocarbon, biodiesel fuel or ethanol fuel; preferably a petroleum hydrocarbon or biodiesel fuel; preferably a petroleum hydrocarbon; preferably crude oil, gasoline, diesel fuel, kerosene, jet fuel or heating oil; preferably gasoline.

Preferably, the marker compounds are detected by at least partially separating them from constituents of the petroleum hydrocarbon or liquid biologically derived fuel using a chromatographic technique, e.g., gas chromatography, liquid chromatography, thin-layer chromatography, paper chromatography, adsorption chromatography, affinity chromatography, capillary electrophoresis, ion exchange and molecular exclusion chromatography. Chromatography is followed by at least one of: (i) mass spectral analysis, and (ii) FTIR. Identities of the marker compounds preferably are determined by mass spectral analysis. Preferably, mass spectral analysis is used to detect the marker compounds in the petroleum hydrocarbon or liquid biologically derived fuel without performing any separation. Alternatively, marker compounds may be concentrated prior to analysis, e.g., by distilling some of the more volatile components of a petroleum hydrocarbon or liquid biologically derived fuel.

Preferably, more than one marker compound is present. Use of multiple marker compounds facilitates incorporation into the petroleum hydrocarbon or liquid biologically derived fuel of coded information that may be used to identify the origin and other characteristics of the petroleum hydrocarbon or liquid biologically derived fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon or liquid biologically derived fuel directly, or alternatively, placed in an additives package containing other compounds, e.g., antiwear additives for lubricants, detergents for gasoline, etc., and the additives package is added to the petroleum hydrocarbon or liquid biologically derived fuel.

The compounds of this invention may be prepared by methods known in the art. For example, substituted benzyl halides may react with Bisphenol A in the presence of base according to the following equation:

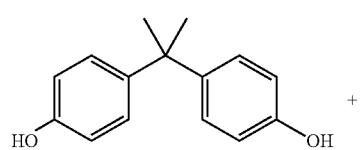

+

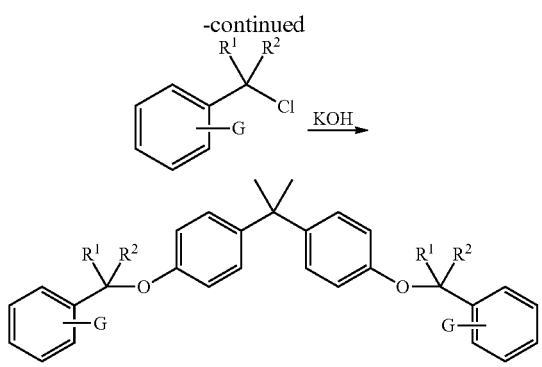

EXAMPLES

Example 1

Preparation of Bisphenol A bis(2-methylbenzyl) ether

Under an inert atmosphere, 5.23 g Bisphenol A (BPA) (22.9 mmol) and 2.83 g potassium hydroxide (50.4 mmol) were dissolved in 50 mL dimethylacetamide. Stirring was started at 500 rpm and the contents were warmed to 70° C. After 30 minutes, 7.09 g 2-methylbenzyl chloride (50.4 mmol) dissolved in 50 mL dimethylacetamide was added to the reaction mixture. The mixture was then heated at 100° C. for 4 h until no 2-methylbenzyl chloride was noted in the GPC trace. During the course of the reaction, a white precipitate had formed. The reaction mixture was cooled to room temperature and then poured into a 1 L separatory funnel containing 200 mL deionized water. The aqueous layer immediately became opaque. The reaction flask was washed with 50 mL deionized water and this wash was added along with 150 mL toluene to the separatory funnel. The separatory funnel was shaken and the bilayer allowed to settle. The lower, aqueous layer appeared opaque while the upper, organic layer was clear and colorless. The organic layer was separated and the aqueous layer was washed 3 additional times with 100 mL toluene. The combined organic fractions were dried over 20 g magnesium sulfate and filtered into a 1 L round bottom flask. The solvent was removed from the filtered toluene solution on a rotary evaporator initially at room temperature then at 70° C. Following solvent removal, a viscous oil remained in the round bottom flask. This crude product was recrystallized at 0° C. from an acetone solution. The crystalline white solid that had formed was filtered on a 7.0 cm Buchner funnel using Whatman 540 filter paper. The crystals were pulverized into a powder and washed with cold acetone. The white powder was transferred to a 75° C. vacuum oven and dried for 24 h. For Bisphenol A bis(2-methylbenzyl) ether: 52% yield (5.2 g, 12 mmol); white powder; mp 117° C. $^1$H NMR (500.1 MHz, CD$_2$Cl$_2$, ppm, J=Hz): 7.40 (d, 7.2, 2H, Ph), 7.23 (m, 6H, Ph), 7.17 (m, 4H, Ph), 6.90 (m, 4H, Ph), 5.02 (s, 4H, -PhC$\underline{H}_2$O—), 2.37 (s, 6H, -PhC$\underline{H}_3$), 1.65 (s, 6H, —C(C$\underline{H}_3$)$_2$).

Example 2

Preparation of Bisphenol A bis(3-methylbenzyl) ether

Prepared according to the procedure of Example 1 from BPA and 3-methylbenzyl chloride-21% yield; colorless oil. $^1$H NMR (500.1 MHz, CD$_2$Cl$_2$, ppm, J=Hz): 7.22-7.29 (m, 6H, Ph), 7.15 (m, 6H, Ph), 6.87 (m, 4H, Ph), 5.00 (s, 4H, -PhC$\underline{H}_2$O—), 2.37 (s, 6H, -PhC$\underline{H}_3$), 1.64 (s, 6H, —C(C$\underline{H}_3$)$_2$).

Example 3

Preparation of Bisphenol A bis(4-methylbenzyl) ether (Composition Known, CAS#87353-49-9)

Prepared according to the procedure of Example 1 from BPA and 4-methylbenzyl chloride-61% yield; white powder; mp 101° C. $^1$H NMR (500.1 MHz, CD$_2$Cl$_2$, ppm, J=Hz): 7.32 (d, 8.1, 4H, Ph), 7.20 (d, 7.9, 4H, Ph), 7.15 (m, 4H, Ph), 6.87 (m, 4H, Ph), 4.99 (s, 4H, -PhC$\underline{H}_2$O—), 2.36 (s, 6H, -PhC$\underline{H}_3$), 1.64 (s, 6H, —C(C$\underline{H}_3$)$_2$).

Example 4

Preparation of Bisphenol A bis(alpha-methylbenzyl) ether

Prepared according to the procedure of Example 1 from BPA and alpha-methylbenzyl chloride-84% yield; gold oil. $^1$H NMR (500.1 MHZ, (CD$_3$)$_2$CO, ppm, J=Hz): 7.42 (m, 4H, Ph), 7.33 (m, 4H, Ph), 7.24 (m, 2H, Ph), 7.01 (m, 4H, Ph), 6.76 (m, 4H, Ph), 5.39 (q, 6.5, 2H, PhC$\underline{H}$(Me)O—), 1.52-1.57 (m, 12H, Me).

Example 5

Demonstration of GC-MS Detectability

Method Evaluation for Ex. 1 Product in DCM:

| Stock | Stock(mg/ml) | SubStock(μg/ml) |
|---|---|---|
| Ex. 1 product | 1.13 | 11.300 |

11.3 mg in 10 ml DCM, 0.25 ml Stock in 25 ml DCM

| Standard | 1 | 2 | 3 | 4 |
|---|---|---|---|---|
| Substock | 200 μl | 400 μl | 600 μl | 800 μl |
| Ex. 1 product (μg/L) | 226 | 452 | 678 | 904 |

Linearity and Accuracy:

| Standard | Conc(ppb) | Area | Conc.(ppb) | % Recovery |
|---|---|---|---|---|
| 1 | 226 | 48058 | 239.8 | 106.1 |
| 1 | 226 | 47839 | 239.1 | 105.8 |
| 2 | 452 | 114210 | 445.2 | 98.5 |
| 2 | 452 | 110243 | 432.9 | 95.8 |
| 3 | 678 | 186029 | 668.3 | 98.6 |
| 3 | 678 | 183055 | 659.0 | 97.2 |
| 4 | 904 | 264936 | 913.3 | 101.0 |
| 4 | 904 | 267871 | 922.4 | 102.0 |

Plotting area against concentration gave a line with slope=321.9825, intercept=−29140 and $R^2$=0.9968

Repeatability and Accuracy:

| | Concentration 226 ppb | | |
|---|---|---|---|
| Rep | Area | Conc.(ppb) | % Recovery |
| 1 | 41152 | 218.3 | 96.6 |
| 2 | 42116 | 221.3 | 97.9 |
| 3 | 45887 | 233.0 | 103.1 |
| 4 | 48805 | 242.1 | 107.1 |
| 5 | 48058 | 239.8 | 106.1 |
| 6 | 47839 | 239.1 | 105.8 |
| Avg. | 45643 | 232.3 | 102.8 |
| Std Dev | 3266 | 10.14 | 4.49 |
| RSD | 7.15 | 4.37 | 4.37 |

Note:
1. SIM: 105
2. Solvent: Dichloromethane (DCM)

The invention claimed is:

1. A compound having formula (I),

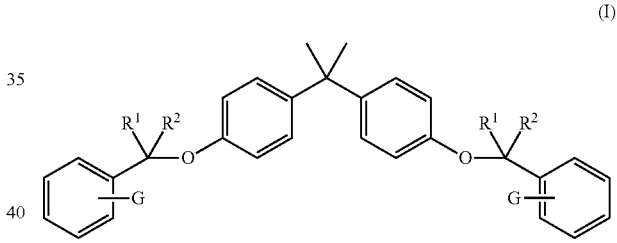

(I)

wherein $R^1$ and $R^2$ independently represent hydrogen or $C_1$-$C_4$ alkyl groups, and G represents hydrogen or at least one substituent selected from the group consisting of $C_1$-$C_{18}$ alkyl and $C_1$-$C_{18}$ alkoxy; provided that when $R^1$ and $R^2$ represent hydrogen, G does not represent hydrogen, 4-methyl, 4-methoxy, 3-methoxy, 2,6-dipropargyl, 4-vinyl, 4-ethynyl or 3-ethynyl; and wherein alkyl groups are saturated and unsubstituted.

2. The compound of claim 1 in which $R^1$ and $R^2$ independently represent hydrogen or methyl.

3. The compound of claim 2 in which G represents hydrogen or at least one substituent selected from the group consisting of $C_1$-$C_8$ alkyl and $C_1$-$C_8$ alkoxy.

4. The compound of claim 3 in which G represents hydrogen or one or two substituents selected from the group consisting of $C_1$-$C_6$ saturated alkyl and $C_1$-$C_6$ saturated alkoxy.

5. The compound of claim 4 in which G represents one or two substituents selected from the group consisting of $C_1$-$C_4$ saturated alkyl and $C_1$-$C_4$ saturated alkoxy.

6. The compound of claim 5 in which G represents one or two substituents selected from the group consisting of methyl and ethyl.

7. A compound having formula (I),

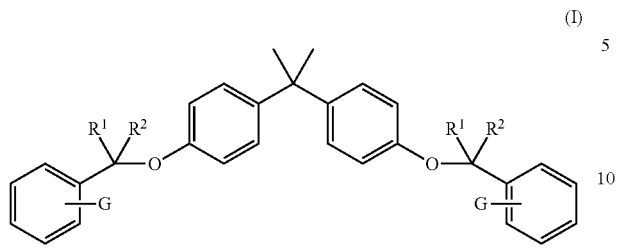

wherein $R^1$ and $R^2$ independently represent hydrogen or $C_1$-$C_4$ alkyl groups, and G represents at least one $C_1$-$C_{18}$ saturated and unsubstituted alkyl substituent, provided G does not represent a single alkyl substituent in the 4-position.

8. The compound of claim 7 in which $R^1$ and $R^2$ independently represent hydrogen or methyl.

9. The compound of claim 8 in which G represents one or two $C_1$-$C_8$ saturated alkyl substituents and $R^1$ and $R^2$ represent hydrogen.

* * * * *